United States Patent [19]
Pond et al.

[11] 4,000,148
[45] Dec. 28, 1976

[54] POLYCHROMOPHORIC HETEROCYCLIC ULTRAVIOLET STABILIZERS AND THEIR USE IN ORGANIC COMPOSITIONS

[75] Inventors: David M. Pond; Richard H. S. Wang; Gether Irick, Jr., all of Kingsport, Tenn.

[73] Assignee: Eastman Kodak Company, Rochester, N.Y.

[22] Filed: Nov. 14, 1974

[21] Appl. No.: 523,628

[52] U.S. Cl. .................... 260/304 R; 106/176; 427/164; 252/300; 260/45.8 N; 260/45.8 NZ; 260/307 D; 260/308 B; 260/326.14 R

[51] Int. Cl.² ............ C07D 263/62; C07D 209/14; C07D 277/66

[58] Field of Search ....... 260/308 B, 307 D, 304 P, 260/304 C, 326.14 R

[56] References Cited
UNITED STATES PATENTS

| | | | |
|---|---|---|---|
| 2,715,630 | 8/1955 | Sartori | 260/304 |
| 2,968,856 | 1/1961 | Allen | 260/304 |
| 3,496,188 | 2/1970 | Wirth | 260/308 B |
| 3,673,202 | 6/1972 | Orlando et al. | 260/304 |
| 3,689,425 | 9/1972 | Crounse | 260/308 B |
| 3,821,240 | 6/1974 | Agbli et al. | 260/307 D |

*Primary Examiner*—R. J. Gallagher
*Attorney, Agent, or Firm*—Clyde L. Tootle; Daniel B. Reece, III

[57] ABSTRACT

The invention relates to polychromophoric heterocyclic ester compounds which have been found to be effective ultraviolet stabilizers. The invention also relates to ultraviolet degradable organic compositions containing a stabilizing amount of these polychromophoric heterocyclic ester compositions to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

20 Claims, No Drawings

POLYCHROMOPHORIC HETEROCYCLIC ULTRAVIOLET STABILIZERS AND THEIR USE IN ORGANIC COMPOSITIONS

This invention relates to polychromophoric heterocyclic ester ultraviolet stabilizers and their use in organic compositions. More particularly, the invention relates to polychromophoric heterocyclic ester compositions and the stabilization of ultraviolet degradable organic compositions against deterioration resulting from the exposure to such radiations with such polychromophoric heterocyclic ester compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet and degradation and deterioration.

It is still another object of the present invention to provide compositions containing polychromophoric compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations, including short wavelength visible radiations.

Further objects and advantages of the invention will be apparent to those skilled in the art from the accompanying disclosure and claims.

In accordance with the present invention, polychromophoric heterocyclic ester compositions are provided which are useful as ultraviolet stabilizers or ultraviolet screening agents. These organic compositions contain at least one heterocyclic group containing composition connected through a carboxyl group to an aromatic ring which, upon exposure to ultraviolet light, may undergo the "photoFries" rearrangement. The polychromophoric compositions of the present invention have the following structure:

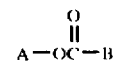

wherein A is a group having the structure:

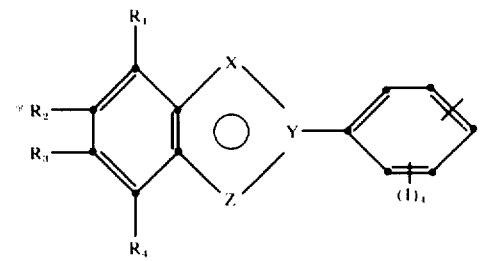

and B is a group having the structure:

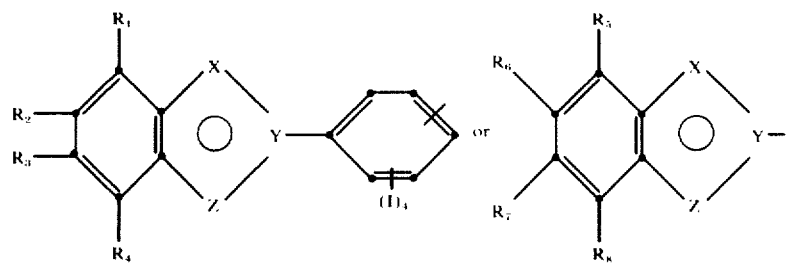

wherein
X and y are a carbon atom or a nitrogen atom;
Z is an oxygen atom, a sulfur atom, a nitrogen atom, a nitrogen atom containing a hydrogen atom or a substituted or unsubstituted lower alkyl group containing 1 to 12 carbon atoms;

$R_1$, $R_2$, $R_3$, $R_4$, $R_5$, $R_6$, $R_7$ and $R_8$ are hydrogen, lower alkyl, substituted lower alkyl, cycloalkyl, substituted cycloalkyl, aryl, halogen, substituted aryl, lower alkylaryl, aryl-substituted-aryl, alkoxy, carboxy, nitrile, and the substituents $R_1$ and $R_2$, $R_2$ and $R_3$, $R_3$ and $R_4$, $R_4$ and $R_5$, $R_5$ and $R_6$, $R_6$ and $R_7$ and $R_8$, combined with the carbon atoms to which they are attached, are joined alkylene groups completing a carbocyclic ring which can be substituted with any of the substituents listed above for $R_1$, $R_2$, $R_3$, $R_4$, $R_5$, $R_6$, and $R_7$.

l is a substituent listed above for $R_1$, $R_2$, $R_3$, $R_4$, $R_5$, $R_6$, $R_7$, and $R_8$ present on all positions of the benzenoid ring, except the carbon atom attached to the Y substituent and the carbon atom attached to the carboxyl group connecting the heterocyclic aromatic A group with the aromatic B group. The carboxyl connecting group is attached to the benzene ring in either the meta or para position from the carbon atom connected to Y or is connected directly to Y. The l substituents can all be one of the substituents listed above or different listed substituents.

Suitable A and B groups having the structure

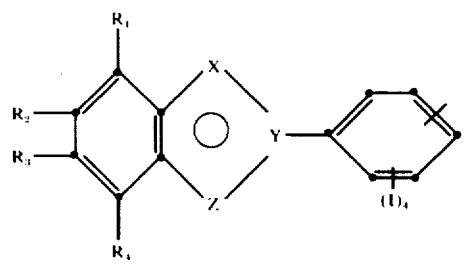

are, for example, substituted and unsubstituted benzoxazoles, benzotriazoles, benzothiazoles, and benzimidazoles.

Examples of such suitable benzoxazole moieties are those having the formula

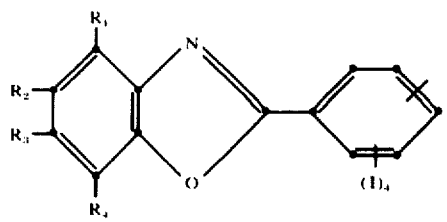

such as 4-(5,6-dimethyl-2-benzoxazolyl)phenyl, 4-(2-benzoxazolyl)-2-chlorphenyl, and 3-(5-chloro-2-benzoxazolyl)phenyl.

Examples of suitable benzotriazole moieties are those having the formula

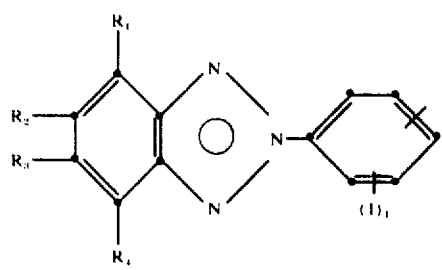

such as substituted and unsubstituted benzotriazoles such as 4-(5-chloro-2H-benzotriazol-2-yl)phenyl, 4-(2H-benzotriazol-2-yl)phenyl, 4-(5-methoxy-2H-benzotriazol-2-yl)phenyl, 2,5-dimethyl-4-(2H-benzotriazol-2-yl)phenyl, 2,5-dimethyl-4-(5-chloro-2H-benzotriazol-2-yl)phenyl, 2-methyl-4-(2H-benzotriazol-2-yl)phenyl, 2-methyl-4-(5-chloro-2H-benzotriazol-2-yl)phenyl, 2-chloro-4-(2H-benzotriazol-2-yl)phenyl, 2,5-dichloro-4-(2H-benzotriazol-2-yl)phenyl, 2-chloro-4-(5-chloro-2H-benzotriazol-2-yl)phenyl, 2,6-dichloro-4-(5-chloro-2H-benzotriazol-2yl)phenyl, 2,6-dimethyl-4-(5-methoxy-2H-benzotriazol-2-yl)phenyl, 2,6-dimethyl-4-(5-methoxy-2H-benzotriazol-2-yl)phenyl, 2,6-dichloro-4-(5-methoxy-2H-benzotriazol-2-yl)phenyl, 2-chloro-4-(5-methoxy-2H-benzotriazol-2-yl)phenyl, 2-methyl-4-(5-methoxy-2H-benzotriazol-2-yl)phenyl 2-phenyl-4-(2H-benzotriazol-2-yl)phenyl, 4-methyl-2-(5-chloro-2H-benzotriazol-2-yl)phenyl, 4-methyl-2-(5-methoxy-2H-benzotriazol-2-yl)phenyl, 4-(4,6-dichloro-2H-benzotriazol-2-yl)phenyl, 4-(4,6-dimethyl-2H-benzotriazol-2-yl)phenyl, 4-methyl-2-(2H-benzotriazol-2-yl)phenyl, and the like.

Examples of suitable benzothiazole moieties are those having the formula

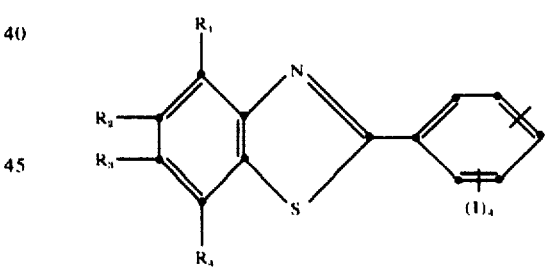

such as 4-(5,6-dimethyl-2-benzothiazolyl)phenyl, 4-(2-benzothiazolyl)-2-chlorophenyl, and 3-(5-chloro-2-benzothiazolyl)phenyl, 2-(2-benzothiazolyl)phenyl, 4-(2-benzothiazolyl)phenyl, and the like.

Examples of suitable benzimidazole moieties are those having the formula

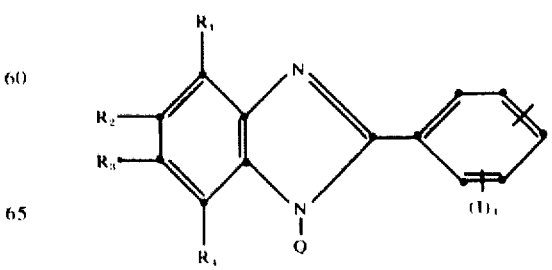

wherein Q is hydrogen or a substituted or unsubstituted lower alkyl group containing 1 to 12 carbon atoms, such as 4-(5,6-dimethyl-2-benzimidazolyl)phenyl, 4-(2-benzimidazolyl)-2-chlorophenyl, 3-(5-chloro-2-benzimidazolyl)phenyl, 4-(1-methyl-2-benzimidazolyl)phenyl, 4-(1-ethyl-5-chloro-2-benzimidazolyl)phenyl, 3-(1-ethyl-2-benzimidazolyl)phenyl, 2(1-(methyl-2-benzimidazolyl)phenyl, and 2-(1-ethyl-5-chloro-2-benzimidazolyl)phenyl.

Examples of suitable indole moieties are those having the formula

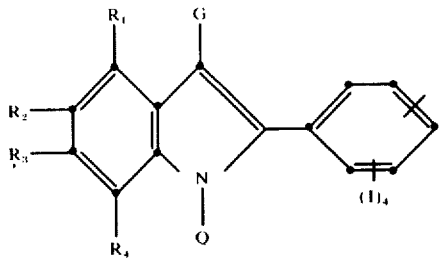

wherein G is the same as $R_1$ and Q is hydrogen or a substituted or unsubstituted lower alkyl containing 1 to 12 carbon atoms, such as 3-(1-ethyl-3-cyano-2-indolyl)phenyl, 3-(5-chloro-2-indolyl)phenyl, 3-(1-methyl-2-indolyl)phenyl, 3-(3-methyl-2-indolyl)phenyl, 3-(3-chloro-2-indolyl)phenyl, 3-(5-acetamido-2-indolyl)phenyl, 3-(2-indolyl)phenyl, 4-(1-ethyl-2-indolyl)phenyl, 4-(3-cyano-2-indolyl)phenyl, 4-(5-methoxy-2-indolyl)phenyl, 4-(1-methyl-2-indolyl)phenyl, 4-3-methyl-5-phenyl-2-indolyl)phenyl, 4-3,5-dichloro-2-indolyl)phenyl, 4-(2-indolyl)phenyl, 4-chloro-2-indolylphenyl, 2-(1-methyl-2-indolyl)phenyl and 2-(1-ethyl-3-cyano-2-indolyl)phenyl.

Suitable B groups having the structure

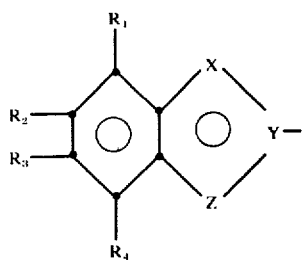

are, for example, substituted and unsubstituted 2-benzoxazolyl, 2-benzothiazolyl, 2-benzimidazolyl and benzotriazolyl.

Examples of suitable 2-benzoxazolyl moieties are those having the formula

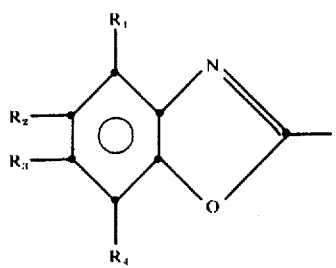

such as 5,6-dimethyl-2-benzoxazolyl, 2-benzoxazolyl, 5-chloro-2-benzoxazolyl, 5,6-dichloro-2-benzoxazolyl, 4,5-diethyl-2-benzoxazolyl, 5-cyano-2-benzoxazolyl, 5-methoxy-6-methyl-2-benzoxazolyl, for 4-chloro5-phenyl-2-benzoxazolyl.

Examples of suitable 2-benzothiazolyl moieties are those having the formula

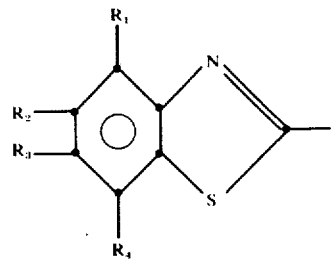

such as 2-benzothiazolyl, 5,6-dimethyl-2-benzothiazolyl, 5,6-dichloro-2-benzothiazolyl, 5-chloro-2-benzothiazolyl, 5-methoxy-2-benzothiazolyl, 6-methylsulfonyl-2-benzothiazolyl, 6-cyano-2-benzothiazolyl, 6-methylthio-2-benzothiazolyl, and 6-methyl-2-benzothiazolyl.

Examples of suitable 2-benzimidazolyl moieties are those having the formula

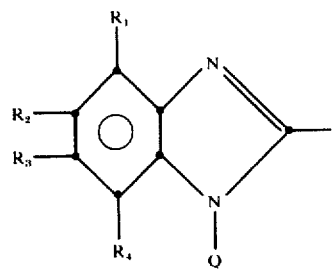

wherein Q is hydrogen or a substituted or unsubstituted lower alkyl containing 1 to 12 carbon atoms, such as 2-benzimidazolyl, 1-methyl-2-benzimidazolyl, 1,5,6-trimethyl-2-benzimidazolyl, 6-cyano-1-ethyl-2-benzimidazolyl, 6-chloro-2-benzimidozolyl, 5-methoxy-1-benzyl-2-benzimidozolyl, 6-methylsulfonyl-2-benzimidazolyl, 4-methoxy-1-methyl-2-benzimidazolyl, and the like.

Examples of suitable 2-indolyl moieties are those having the formula

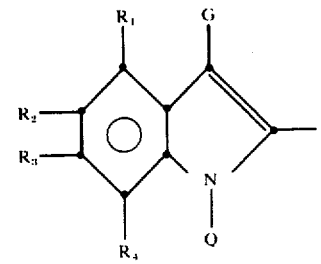

wherein G is the same as $R_1$ and
Q is hydrogen or a substituted or unsubstituted lower alkyl containing 1 to 12 carbon atoms. Such suitable indole moieties are, for example, 1-ethyl-3-cyano-2-indolyl, 5-chloro-2-indolyl, 1-methyl-2-indolyl, 3-methyl-2-indolyl, 3-chloro-2-indolyl, 5-acetamido-2-indolyl, 1-benzyl-2-indolyl, 3-cyano-2-indolyl, 5-methoxy-2-indolyl, 1-methyl-2-indolyl, 3-methyl-5-phenyl-2-indolyl, 3,5-dichloro-2-indolyl and 2-indolyl.

The polychromophoric heterocyclic ester compositions can be prepared by reacting an acid chloride with a phenol. For example, one group of such organic compounds useful as ultraviolet stabilizers is, for example, compositions having the following structures One method for preparing these compounds is by the following procedure:

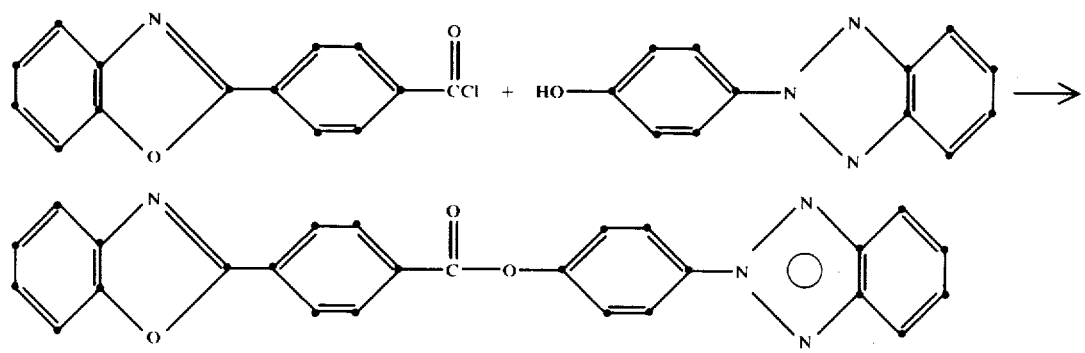

It is necessary that at least one carbon atom adjacent to the carbon atom attached to the carboxy oxygen contain a hydrogen substituent so that on exposure to ultraviolet light, the aryl ester is capable by the "photo-Fries" rearrangement of forming a phenol group in that position formerly joined through an oxygen atom to the carbonyl linking group, as for example:

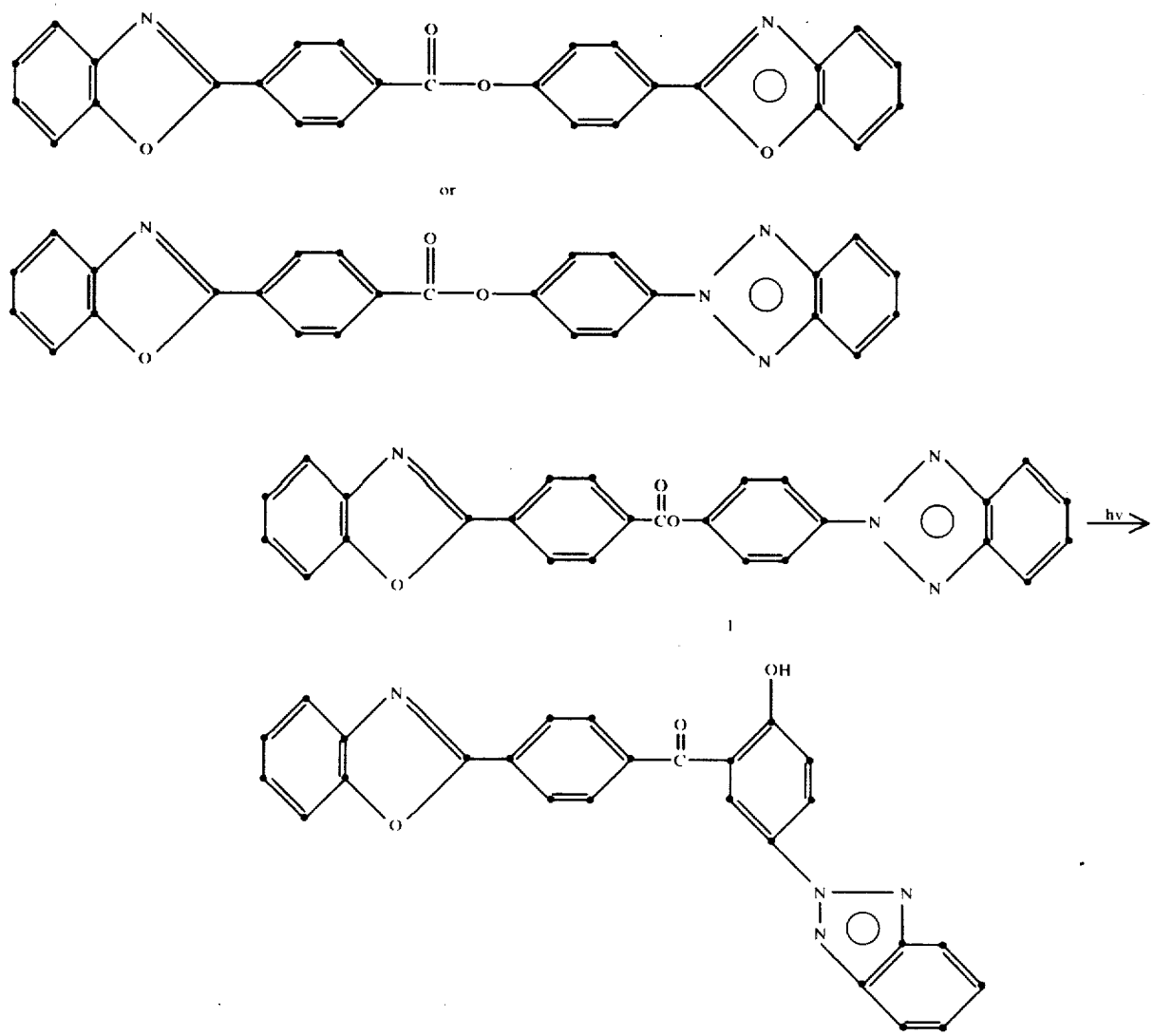

The acid chlorides were prepared by reaction of the corresponding acid [See *Zh. Obshch. Khim.*, 38, 100 1-5 (1968); *Chem. Abstr.* 69 96568 (1968)] with freshly distilled thionyl chloride [See *J. Chem. Soc.* 101, 2476 (1912)]. The phenols were obtained from commercial sources, or were prepared by standard methods; a critical requirement is that one of the positions adjacent the phenolic hydroxyl group be unsubstituted.

The heterocyclic compositions can be added to organic compositions which are susceptible to ultraviolet degradation. Such compositions include, for example, polymeric compositions such as polyester fiber and molding compositions, such as polyethylene terephthalate, poly(tetramethylene terephthalate) and the like; polyolefins such as, for example, high, medium and low density polyethylene, polypropylene, polybutene and the like; polyamides such as nylon 6, nylon 66, N-methoxymethyl polyhexamethylene adipamide and the like; polycarbonates; polyvinyl chlorides and co-polymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals, polyformaldehydes; and polyurethanes. Such compositions also include natural and synthetic rubbers, such as polybutadiene, and unsaturated organic compositions such as oils and the like, as well as compositions containing such organic compositions.

The polychromophoric compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate and polyester such as poly(tetramethylene terephthalate) plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel polychromophoric ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1 p-(2H-benzotriazole-2-yl)phenyl 4-(2-benzoxazolyl) benzoate (1) can be prepared by the following procedure:

o-Nitroaniline (0.5 mole) was diazotized in the usual manner with concentrated hydrochloric acid (200 ml.) and sodium nitrite (0.5 mole). The clear diazonium solution was added slowly to a cold solution (0°–5° C.) of phenol (0.5 mole) in 450 ml. of 10% sodium hydroxide. The mixture was stirred for 1 hour and compound A filtered out (60% yield). One-tenth mole of compound A was dissolved in 100 ml. of 2N NaOH. Zinc dust (30 g.) and sodium hydroxide (50 ml. of a 25% solution) were added slowly to the well-stirred solution to keep the temperature below 45° C. The mixture was then cooled to <30° C. and acidified with concentrated hydrochloric acid. After stirring for 2 hours, the precipitate was filtered. Recrystallization from ethanol-water gave p-(2H-benzotriazol-2-yl)phenol (B) in 90% yield (mp 216°–218°).

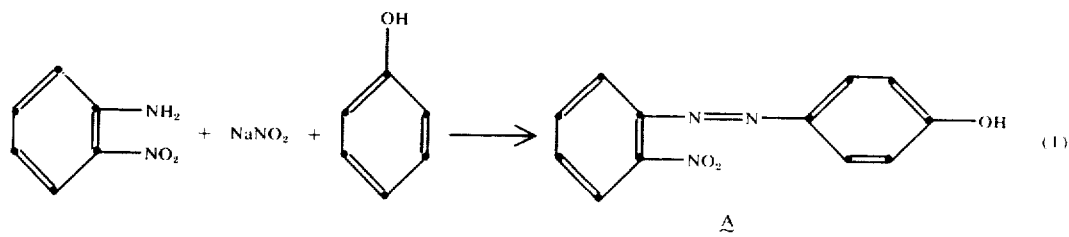

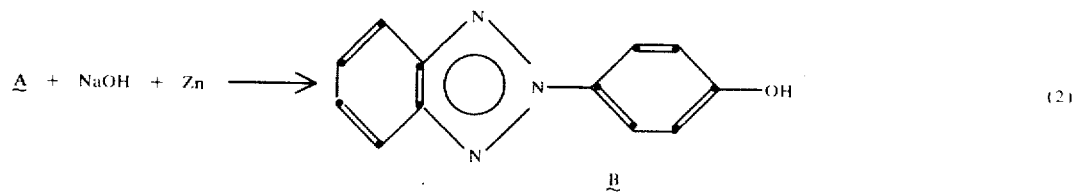

To a solution of 0.8 g. (0.02 mole) of sodium hydroxide in 50 ml. of water was added 4.22 g. (0.02 mole) of B. The mixture was stirred for 10 minutes and 150 ml. of chloroform 5.16 g. (0.02 mole) of 4-(2-benzoxazolyl)benzoyl chloride was added dropwise. The mixture was stirred at reflux for 15 hours after the addition was completed. The reaction mixture was cooled to 30°C. and a solid separated and between the layers. This was filtered and air-dried and amounted to 8.0 g. (93%) of 1 (mp 295°–300°).

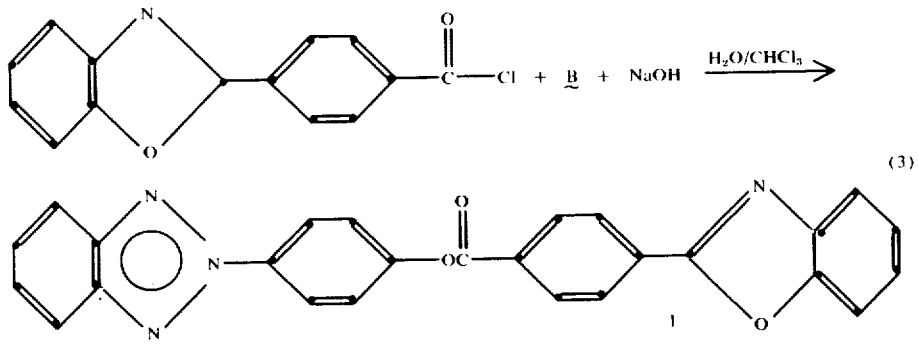

Other novel polychromophoric compounds can be prepared by substitution of other benzotriazoles for 4-(2H-benzotriazol-2-yl)-2,5-dimethylphenol, 4-(5-chloro-2H-benzotriazol-2-yl)phenyl, 4-(5-methyl-2H-benzotriazol-2-yl)-2,5-dimethylphenol, 4-(5-methyl-2H-benzotriazol-2-yl)-2-methylphenol, 4-(5-chloro-2H-benzotriazol-2-yl)-2-methylphenol, 4-(2H-benzotriazol-2-yl)-2-methylphenol, 4-(2H-benzotriazol-2-yl)-2-chlorophenol, 4-(5-chloro-2H-benzotriazol-2-yl)-2-chlorophenol, 4-(5-methyl-2H-benzotriazol-2-yl)-2-chlorophenol, 4-(2H-benzotriazol-2-yl)-2,5-dimethoxyphenol, 4-(5-chloro-2H-benzotriazol-2-yl)-2,5-dimethoxyphenol, 4-(5-methyl-2H-benzotriazol-2-yl)-2,5-dimethoxyphenol, 4-(2H-benzotriazol-2-yl)-2-methoxyphenyl, 4-(5-chloro-2H-benzotriazol-2-yl)-2-chlorophenol, and 4-(5-methyl-2H-benzotriazol-2-yl)-2-methoxyphenol.

Also, other polychromophoric compounds can be prepared by substituting other benzoxazolylbenzoyl chlorides, such as 4-(5,6-dimethyl-2-benzoxazolyl)-benzoyl chloride, 4-(2-benzoxazolyl)-2-chlorobenzoyl chloride, 3-(5-chloro-2-benzoxazolyl)benzoyl chloride, 4-(5,6-dichloro-2-benzoxazolyl)benzoyl chloride, 4-(5,6-diethyl-2-benzoxazolyl)benzoyl chloride, 4-(5-cyano-2-benzoxazolyl)benzoyl chloride, 4-(5-methoxy-6-methyl-2-benzoxazolyl)benzoyl chloride, for 4-(2-benzoxazolyl)benzoyl chloride.

EXAMPLE 2

4-(2H-Benzotriazol-2-yl)phenyl 4-(2H-benzotriazol-2-yl)benzoate can be prepared by the reaction of 4-(2H-benzotriazol-2-yl)phenol with 4-(2H-benzotriazol-2-yl)benzoyl chloride by the procedure of Example 1 as follows:

10.5 g. (0.05 mole) 4-(2H-benzotriazol-2-yl)phenol was added to a solution containing 2.0 g. (0.05 mole) sodium hydroxide in 50 ml. of water. A solution of 12.8 g. (0.05 mole) of 4-(2H-benzotriazol-2-yl)benzoyl chloride in 150 ml. of chloroform was added and the resulting solution was refluxed for 13 hr. The product separated out between the layers and was isolated by filtration.

Other phenyl benzotriazolylbenzoates can be prepared by substituting other 2H-benzotriazolylbenzoyl chlorides such as 4-(5,6-dimethyl-2H-benzotriazol-2-yl)benzoyl chloride, 4-(2H-benzotriazol-2-yl)-2-chlorobenzoyl chloride, 3-(5-chloro-2H-benzotriazol-2-yl)benzoyl chloride, 2-(2H-benzotriazole-2-yl)benzoyl chloride, and 4-(5-methoxy-2H-benzotriazol-2-yl)benzoyl chloride, for 4-(2H-benzotriazol-2-yl)benzoyl chloride.

Also, other esters can be prepared by the substitution of other heterocyclic phenols for 4-(2H-benzotriazol-2-yl)phenol, such as 4-(5-chloro-2H-benzotriazol-2-yl)phenol, 4-(5-chloro-2H-benzotriazol-2-2,5-dimethylphenol, 4-(5-methyl-2H-benzotriazol-2-yl)-2,5-yl)phenol, 4-(5-methyl-2H-benzotriazol-2-yl)-2,5-dimethylphenol, 4-(5-methyl-2H-benzotriazol-2-yl)-2-dimethylphenol, 4-(5-chloro-2H-benzotriazol-2-yl)-2-methylphenol, 4-(5-chloro-2H-benzotriazol-2-yl)-2-methylphenol, 2-(2H-benzotriazol-2-yl)-4-methylphenol, 2-(2H-benzotriazol-2-yl)-4-chlorophenol, 2-(5-chloro-2H-benzotriazol-2-yl)-4-methylphenol, 4-(5-methyl-2H-benzotriazol-2-yl)-2-chlorophenol, 2-(2H-benzotriazol-2-yl)-3,5-dimethylphenol, 4-(5-chloro-2H-benzotriazol-2-yl)-2,5-dimethoxyphenol, 4-(5-methyl-2H-benzotriazol-2-yl)-2,5-dimethoxyphenol, 4-(2H-benzotriazol-2-yl)-2-methoxyphenol, 2-(5-chloro-2H-benzotriazol-3,5-di-t-butylphenol, 2-(2H-benzotriazol-2-yl)-3,5-di-t-amylphenol, 2-(2-benzoxazolyl)phenol, 4-(2-benzoxazolyl)phenol, and 2-(2-benzothiazolyl)phenol.

EXAMPLE 3

4-(2H-benzotriazol-2-yl)phenyl, 4-(2-benzothiazolyl)benzoate can be similarly prepared by the procedure of Example 1 as follows:

10.6 g. p-(2H-benzotriazol-2-yl)phenol (0.05 mole) was added to a solution of 2.0 g. (0.05 mole) sodium hydroxide in 200 ml. of water. A solution of 13.7 g. (0.05 mole) of 4-(2-benzothiazolyl)benzoyl chloride was added and refluxing continued for 15 hours after the addition was completed. The reaction mixture was cooled to 30° C. and a solid that had formed between the layers was separated and air-dried.

Other aromatic benzothiazolylbenzoates can be prepared by substituting other benzothiazolylbenzoyl chlorides, such as 4-(5,6-dimethyl-2-benzothiazolyl)benzoyl chloride, 4-(2-benzothiazolyl)-2-chlorobenzoyl chloride, 3-(5-chloro-2-benzothiazolyl)benzoyl chloride, 4-(5,6-dichloro-2-benzothiazolyl)benzoyl chloride, 4-(5,6-diethyl-2-benzothiazolyl)benzoyl chloride, 4-(5-cyano-2-benzothiazolyl)benzoyl chloride, 4-(5-methoxy-6-methyl-2-benzothiazolyl)benzoyl chloride, 3-(2-benzothiazolyl)benzoyl chloride, 2-(2-benzothiazolyl)benzoyl chloride, for 4-(2-benzothiazolyl)-benzoyl chloride.

Also, other esters can be prepared by substitution of other heterocyclic phenols for 4-(2H-benzotriazol-2-yl)phenol, such as 4-(5-chloro-2H-benzotriazol-2-yl)phenol, 4-(5-chloro-2H-benzotriazol-2-yl)-2,5-dimethylphenol, 4-(5-chloro-2H-benzotriazol-2- yl)phenol, 4-(5-methyl-2H-benzotriazol-2-yl)-2,5-dimethylphenol, 2-(5-chloro-2H-benzotriazol-2-yl)phenol, 2-(5-chloro-2H-benzotriazol-2-yl)-3,5-di-t-butylphenol, 2-(2H-benzotriazol-2-yl)-3,5-di-t-butylphenol, 4-(5-methyl-2H-benzotriazol-2-yl)-2-methylphenol, 4-(5-chloro-2H-benzotriazol-2-yl)-2-methylphenol, 4-(2H-benzotriazol-2-yl)-2-methylphenol, 4-(2H-benzotriazol-2-yl)-2-chlorophenol, 4-(5-chloro-2H-benzotriazl-2-yl)-2-chlorophenol, 4-)5-methyl-2H-benzotriazol-2-yl)-2-chlorophenol, 2(2-benzoxazolyl)-phenol, 2-(2-benzothiazolyl)phenol, 4-(2-benzoxazolyl)phenol, 3-(2-benzoxazolyl)phenol, 4-(2H-benzotriazol-2-yl)-2-methoxyphenol, 4-(5-chloro-2H-benzotriazol-2-yl)-2-chlorophenol, and 4-(5-methyl-2H-benzotriazol-2-yl)-2-methoxyphenol.

EXAMPLE 4

4-(2-Benzoxazolyl)phenyl 4-(2-benzimidazolyl)benzoate can be similarly prepared by the procedure of Example 1 as follows:

A mixture containing 5.45 g. (0.05 mole) of o-aminophenol and 6.10 g. (0.05 mole) of p-hydroxybenzaldehyde in 75 ml. of nitrobenzene was heated to reflux for 5 hr. On cooling to 30° a dark solid appears which was filtered, washed with hot toluene, and air-dried. Recrystallization from ethanol gave a 73% yield of 4-(2-benzoxazolyl)phenol (mp 255°–258°).

10.6 g. (0.05 mole) of 4-(2-benzoxazolyl)phenol was mixed with 2.0 g. (0.05 mole) of sodium hydroxide in 75 ml. of water. A solution containing 12.8 g. (0.05 mole) of 4-(2-benzimidazolyl)benzoyl chloride in 125 ml. of chloroform was added and the resulting mixture was refluxed for 10 hr. The product separated between the layers as the reaction proceeded.

Other phenyl benzimidazolylbenzoates can be prepared by substituting other benzimidazolylbenzoyl chlorides, such as 4-(5,6-dimethyl-2-benzimidazolyl)-benzoyl chloride, 4-(2-benzimidazolyl)-2-chlorobenzoyl chloride, 3-(5-chloro-2-benzimidazolyl)benzoyl chloride, 4-(5,6-dichloro-2-benzimidazolyl)benzoyl chloride, 4-(5,6-diethyl-2-benzimidazolyl)benzoyl chloride, 4-(5-cyano-2-benzimidazolyl)benzoyl chloride, 4-(5-methoxy-6-methyl-2-benzimidazolyl)benzoyl chloride, for 4-(2-benzimidazolyl)benzoyl chloride.

Also, other esters can be prepared by substituting other heterocyclic phenols for 4-(2-benzoxazolyl)-phenols, such as 4-(5-chloro-2H-benzotriazol-2-yl)-2,5-dimethylphenol, 4-(5-chloro-2H-benzotriazol-2-yl)phenol, 4-(5-methyl-2H-benzotriazol-2-yl)-2,5-dimethylphenol, 4-(2H-benzotriazol-2-yl)phenol, 4-(5-methyl-2H-benzotriazol-2-yl)-2-methylphenol, 2-(2-benzoxazolyl)phenol, 2-(2-benzothiazolyl)phenol, 4-(5-chloro-2H-benzotriazol-2-yl)-2-methylphenol, 2-(2H-benzotriazol-2-yl)-4-methylphenol, 2-(2H-benzotriazol-2-yl)-4-chlorophenol, 2-(5-chloro-2H-benzotriazol-2-yl)-3,5-di-t-butylphenol, 4-(5-methyl-2H-benzotriazol-2-yl)-2-chlorophenol, 4-(2-benzotriazol-2-yl)-2,5-dimethoxyphenol, 4-(5-chloro-2H-benzotriazol-2-yl)-3,5-di-t-amylphenol, 4-(5-methyl-2H-benzotriazol-2-yl)-2,5-dimethoxyphenol, 4-(2H-benzotriazol-2-yl)-2-methoxyphenol, 4-(5-chloro-2H-benzotriazol-2-yl)-2-chlorophenol, and 4-(5-methyl-2H-benzotriazol-2-yl)-2-methoxyphenol, 2-(2H-benzotriazol-2-yl)-3,5-di-t-amylphenol.

EXAMPLE 5

4-(2H-Benzotriazol-2-yl)phenyl 4-(2-indolyl)benzoate can be similarly prepared by the procedure of Example 1 as follows:

10.6 g. 4-(2H-benzotriazol-2-yl)phenol (0.05 mole) was added to a solution of 2.0 g. (0.05 mole) sodium hydroxide in 50 ml. of water. A solution of 12.79 g. (0.05 mole) of 4-(2-indolyl)benzoyl chloride was added and refluxing continued for 12 hours after the addition was completed. The reaction mixture was cooled at 30° C. and the chloroform layer separated and washed with water until neutral. The solvent was concentrated to about one-half the original volume, chilled and the crude product collected by filtration.

Other phenyl indolylbenzoates can be prepared by substituting other 2-indolylbenzoyl chlorides, such as 4-(5,6-dimethyl-2-indolyl)benzoyl chloride, 4-(2-indolyl)-2-chlorobenzoyl chloride, 3-(5-chloro-2-indolyl)benzoyl chloride, 4-(5-dichloro-2-indolyl)-benzoyl chloride, 4-(5,6-diethyl-2-indolyl)benzoyl chloride, 4-(5-cyano-2-indolyl)benzoyl chloride, 4-(5-methoxy-6-methyl-2-indolyl)benzoyl chloride, for 4-(2-indolyl)benzoyl chloride.

Other novel polychromophoric compounds can be prepared by substitution of other heterocyclic phenols for 4-(2H-benzotriazol-2-yl)phenol, such as 4-(5-chloro-2H-benzotriazol-2-yl)-2,5-dimethylphenol, 4-(5-chloro-2H-benzotriazol-2-yl)-2,5-dimethylphenol, 4-(5-chloro-2H-benzotriazol-2-yl)phenol, 4-(5-methyl-2H-benzotriazol-2-yl)-2,5-dimethylphenol, 2-(2H-benzotriazol-2-yl)-4-methylphenol, 4-(5-methyl-2H-benzotriazol-2-yl)-2-methylphenol, 4-(5-chloro-2H-benzotriazol-2-yl)-2-methylphenol, 4-(2H-benzotriazol-2-yl)-2-methylphenol, 4-(2H-benzotriazol-2-yl)-2-chlorophenol, 4-(5-chloro-2H-benzotriazol-2-yl)-2-chlorophenol, 4-(5-methyl-2H-benzotriazol-2-yl)-2-chlorophenol, 4-(2H-benzotriazol-2-yl)-2,5-dimethoxyphenol, 2-(2-benzoxazolyl)phenol, 2-(5-chloro-2H-benzotriazol-2-yl)-3,5-di-t-butylphenol, 4-(5-methyl-2H-benzotriazol-2-yl)-2,5-dimethoxyphenol, 2-(2H-benzotriazol-2-yl)-3,5-di-t-amylphenol, 4-(5-chloro-2H-benzotriazol-2-yl)-2-chlorophenol, and 4-(5-methyl-2H-benzotriazol-2-yl)-2-methoxyphenol.

These polychromophoric compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

Weathering data results shown in Table 1 illustrate the stabilization obtained with the compounds of this invention.

Table 1

| Additive (0.5%)[a] | Weathering of Poly(tetramethylene terephthalate) Containing 0.5% of Various Stabilizers Flatwise Impact Strength After Mercury Lamp Exposure For Hours Indicated | | |
|---|---|---|---|
| | 0 | 300 | 500 |
| None | 19 | 6 | 1 |
| 2-{2-[4-(2-benzotriazolyl)benzoyloxy]-5-methylphenyl}-benzotriazole | 19 | 19 | 18 |
| 2-{4-[4-(2-benzotriazolyl)benzoyloxy]phenyl}benzotriazole | 20 | 19 | 19 |
| 2-{4-[4-(2-benzoxazolyl)benzoyloxy]phenyl}benzotriazole | 19 | 17 | 18 |
| 2-{2-[4-(2-benzoxazolyl)benzoyloxy]-5-methylphenyl}-benzotriazole | 19 | 19 | 18 |
| 2-{2-[4-(2-benzothiazolyl)benzoyloxy]-5-methylphenyl}-benzotriazole | 21 | 18 | 17 |
| 2-{4-[4-(2-benzoxazolyl)benzoyloxy]phenyl}benzoxazole | 19 | 18 | 19 |
| 2-{4-[4-(2-benzoxazolyl)carbonyloxy]phenyl}-benzoxazole | 18 | 18 | 16 |
| 2-{4-[4-(2-benzothiazolyl)carbonyloxy]phenyl}-benzotriazole | 20 | 19 | 18 |
| 2-{4-[4-(2-benzothiazolyl)benzoyloxy]phenyl}benzoxazole | 20 | 19 | 17 |
| 2-{4-[4-(1-methyl-2-benzimidazolyl)benzoyloxy]phenyl}-benzothiazole | 19 | 19 | 18 |
| 2-{4-[4-(2-benzothiazolyl)benzoyloxy]phenyl}benzotriazole | 19 | 18 | 18 |
| 2-{4-[4-(2-benzimidazolyl)benzoyloxy]phenyl benzotriazole | 19 | 19 | 19 |
| 2- 4-[4-(1-methyl-2-benzimidazolyl)benzoyloxy]phenyl}-benzotriazole | 20 | 19 | 16 |
| 2-{2-[4-(2-benzimidazolyl)benzoyloxy]-5-methylphenyl}-benzotriazole | 20 | 19 | 15 |
| 2-{2-[4-(2-benzotriazolyl)benzoyloxy]phenyl}benzoxazole | 19 | 18 | 18 |
| 2-{2-[4-(2-benzoxazolyl)benzoyloxy]-phenyl}benzoxazole | 20 | 19 | 18 |
| 2-{2-[4-(2-benzoxazolyl)benzoyloxy]-phenyl}benzothiazole | 20 | 19 | 17 |
| 2-{2-[4-(2-benzimidazolyl)benzoyloxy]phenyl}benzothiazole | 19 | 19 | 19 |
| 2-{4-[4-(2-benzimidazolyl)benzoyloxy]phenyl} benzoxazole | 18 | 19 | 18 |

[a]Additives incorporated by blending the powdered additive and granulated polymer, extrusion, pelletization and injection molding into 1/16 × 1/2 × 2 1/2" flat bars. Flatwise impact strengths were determined by ASTM Procedure D256-56 Method A.

The invention has been described in detail with particular reference to preferred embodiments thereof, but it will be understood that variations and modifications can be effected within the spirit and scope of the invention.

We claim:

1. A composition of matter comprising aromatic ester compounds having the formula:

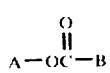

wherein A is a group having the structure:

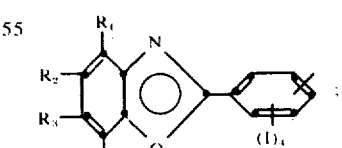

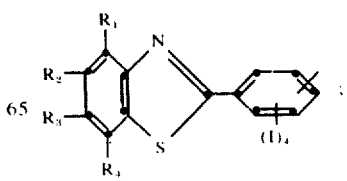

-continued

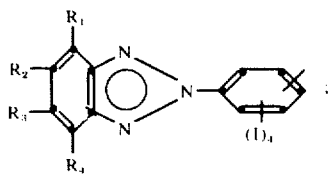

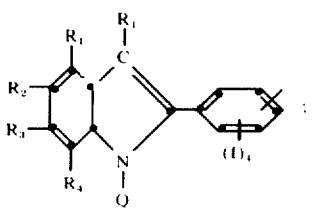

or

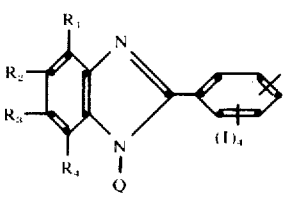

and B is a group having the structure:

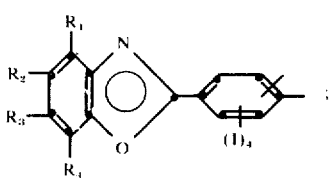

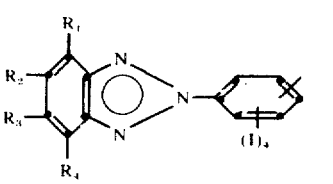

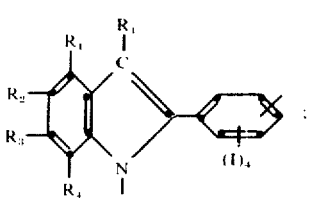

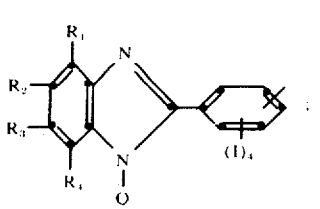

-continued

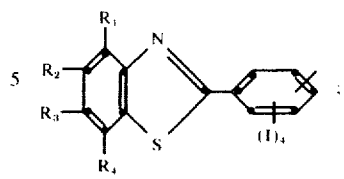

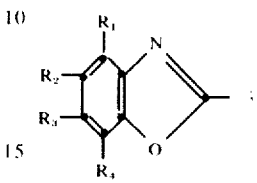

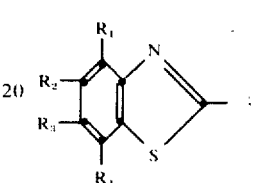

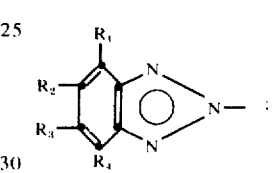

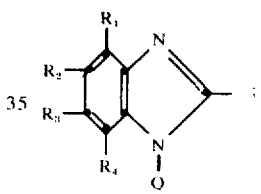

or

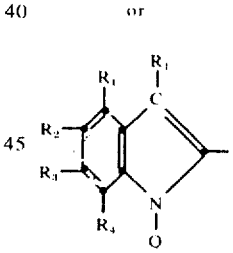

wherein

Q is a hydrogen atom or an alkyl group having 1 to 12 carbon atoms;

$R_1$, $R_2$, $R_3$, and $R_4$, are hydrogen, lower alkyl, phenyl, chlorine, bromine, lower alkyl phenyl, lower alkyloxy, carboxy, nitrile;

I is the same as $R_1$, $R_2$, $R_3$, and $R_4$, and is present on all positions of the benzenoid ring, except the carbon atom attached to the Y substituent and the carbon atoms attached to the carboxyl group connecting the heterocyclic aromatic A group with the heterocyclic aromatic B group.

2. A composition of matter according to claim 1 having the formula:

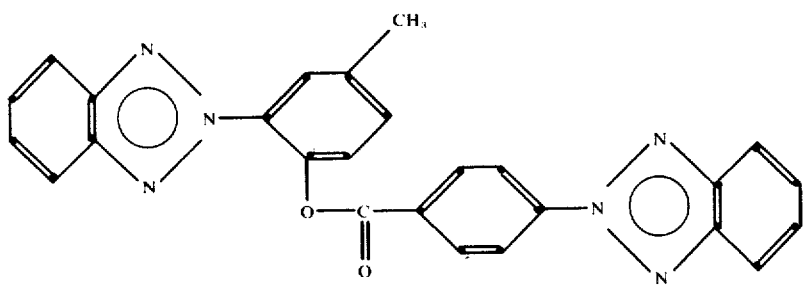
3. A composition of matter according to claim 1 having the formula:
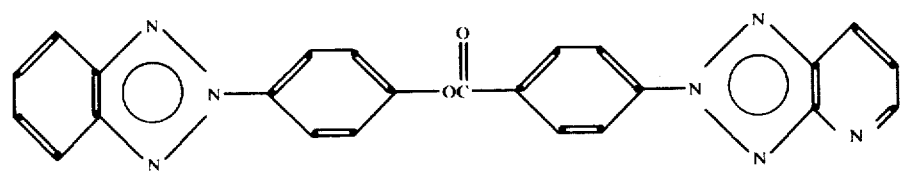
4. A composition of matter according to claim 1 having the formula:
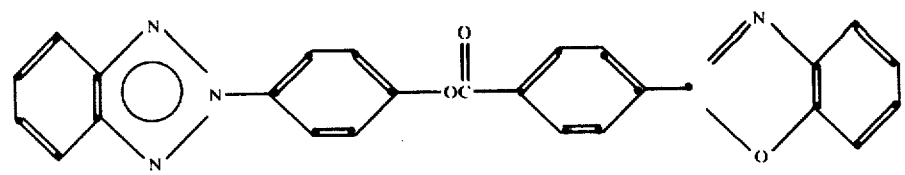
5. A composition of matter according to claim 1 having the formula:
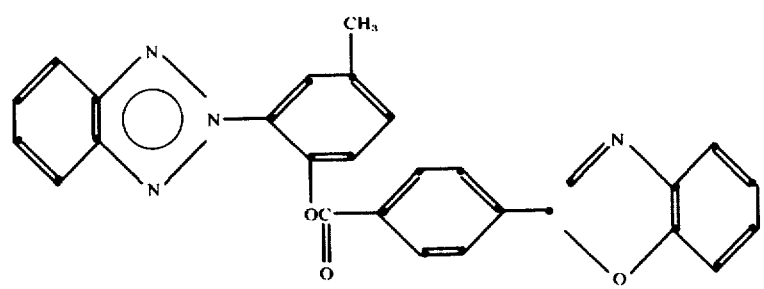
6. A composition of matter according to claim 1 having the formula:
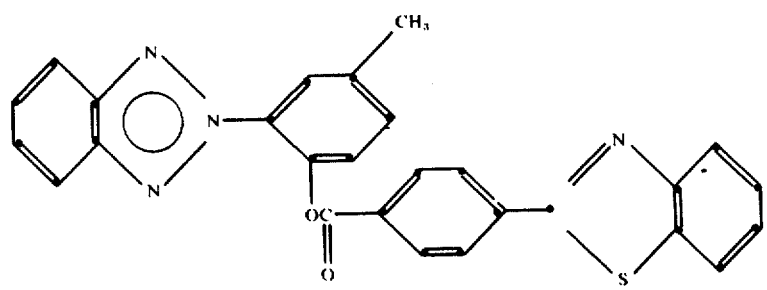
7. A composition of matter according to claim 1 having the formula:

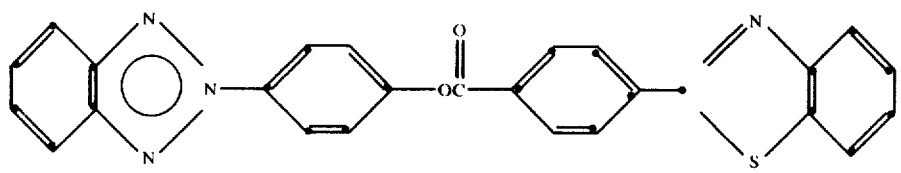
8. A composition of matter according to claim 1 having the formula:
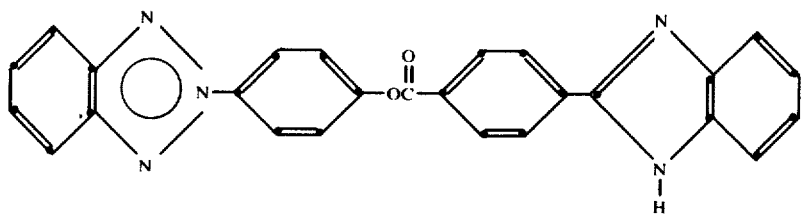
9. A composition of matter according to claim 1 having the formula:
10. A composition of matter according to claim 1 having the formula:
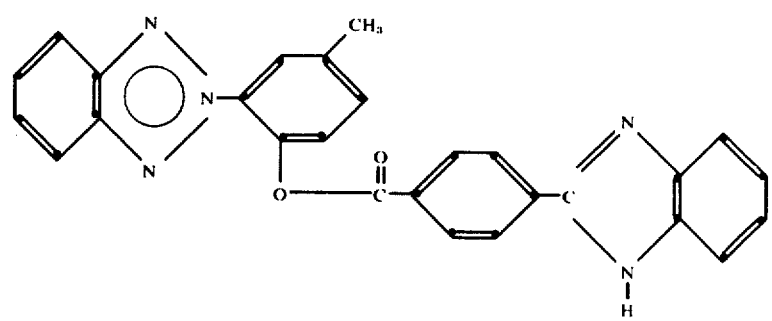
11. A composition of matter according to claim 1 having the formula:
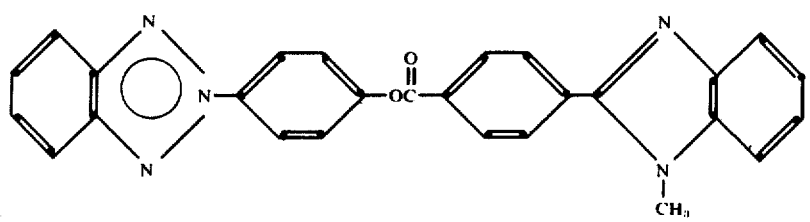
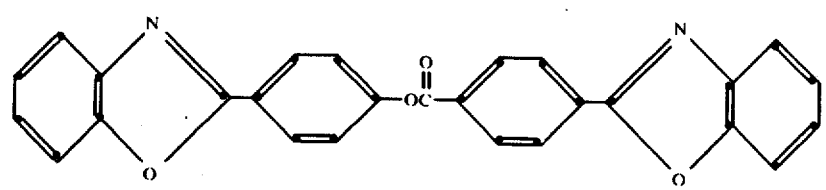
12. A composition of matter according to claim 1 having the formula:

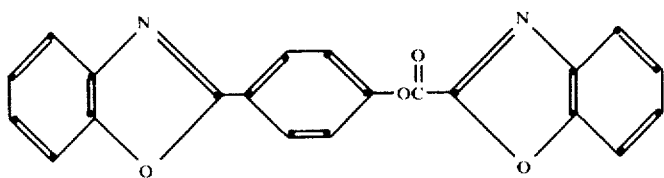

13. A composition of matter according to claim 1 having the formula:

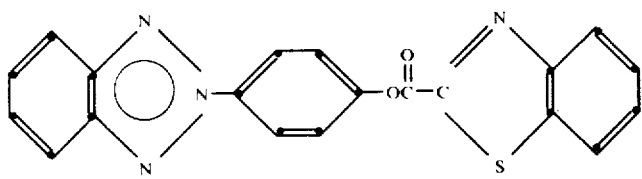

14. A composition of matter according to claim 1 having the formula:

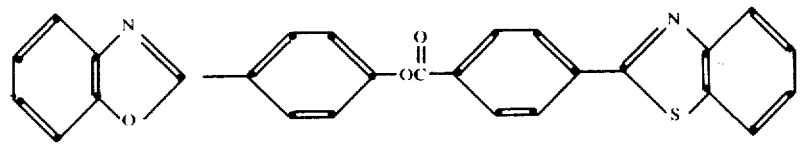

15. A composition of matter according to claim 1 having the formula:

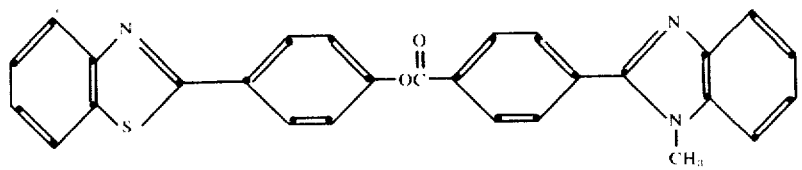

16. A composition of matter according to claim 1 having the formula:

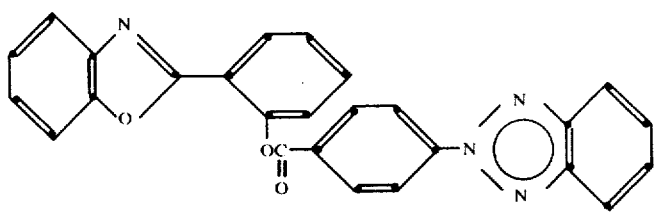

17. A composition of matter according to claim 1 having the formula:

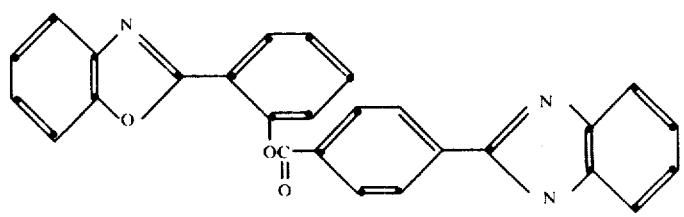

18. A composition of matter according to claim 1 having the formula:

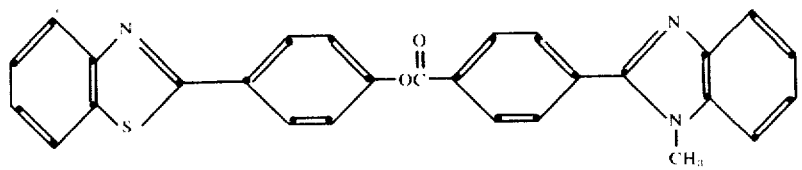

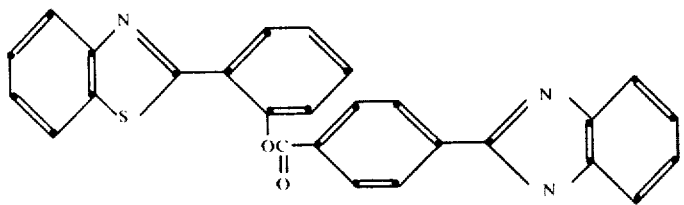
19. A composition of matter according to claim 1 having the formula:
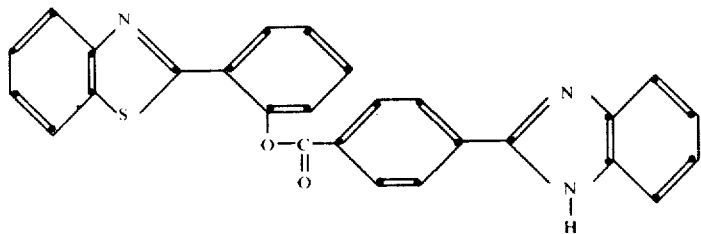
20. A composition of matter according to claim 1 having the formula:
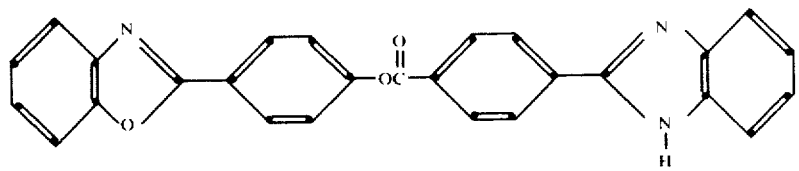
* * * * *

UNITED STATES PATENT OFFICE
CERTIFICATE OF CORRECTION

Patent No. 4,000,148    Dated   December 28, 1976

Inventor(s)   David M. Pond, Richard H. S. Wang, Gether Irick, Jr.

It is certified that error appears in the above-identified patent and that said Letters Patent are hereby corrected as shown below:

Column 24, line 34, after "17", delete "a" and insert therefor ---A---.

Column 25, lines 1-10, delete the formula of Claim 18 and insert therefor

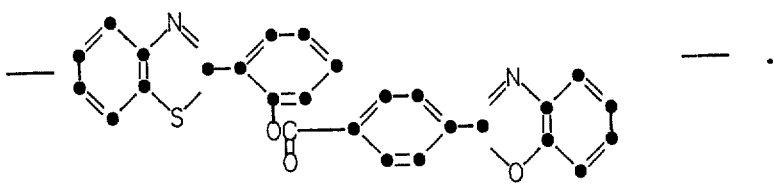

Signed and Sealed this

Twenty-seventh Day of June 1978

[SEAL]

Attest:

RUTH C. MASON
Attesting Officer

DONALD W. BANNER
Commissioner of Patents and Trademarks